(12) United States Patent
Chen et al.

(10) Patent No.: US 8,895,469 B2
(45) Date of Patent: Nov. 25, 2014

(54) ALUMINA SUPPORT, A PROCESS FOR PREPARING THE SUPPORT, A SILVER CATALYST PREPARED FROM THE SUPPORT, AND USE THEREOF

(75) Inventors: Jianshe Chen, Beijing (CN); Jun Jiang, Beijing (CN); Shujuan Wang, Beijing (CN); Zhixiang Zhang, Beijing (CN); Jinbing Li, Beijing (CN)

(73) Assignees: China Petroleum & Chemical Corporation, Beijing (CN); Beijing Research Institute of Chemical Industry, China Petroleum & Chemical Corporation, Beijing (CN)

( * ) Notice: Subject to any disclaimer, the term of this patent is extended or adjusted under 35 U.S.C. 154(b) by 345 days.

(21) Appl. No.: 13/287,720

(22) Filed: Nov. 2, 2011

(65) Prior Publication Data
US 2012/0108832 A1 May 3, 2012

(30) Foreign Application Priority Data
Nov. 2, 2010 (CN) .......................... 2010 1 0534019

(51) Int. Cl.
| | | |
|---|---|---|
| B01J 21/00 | (2006.01) | |
| B01J 23/00 | (2006.01) | |
| B01J 25/00 | (2006.01) | |
| B01J 29/00 | (2006.01) | |
| B01J 20/00 | (2006.01) | |
| B01J 23/68 | (2006.01) | |
| B01J 35/10 | (2006.01) | |
| B01J 37/08 | (2006.01) | |
| B01J 37/00 | (2006.01) | |
| B01J 21/04 | (2006.01) | |
| B01J 37/06 | (2006.01) | |
| C07D 301/10 | (2006.01) | |
| B01J 37/02 | (2006.01) | |
| B01J 35/02 | (2006.01) | |
| B01J 35/00 | (2006.01) | |

(52) U.S. Cl.
CPC ............ *C07D 301/10* (2013.01); *B01J 23/688* (2013.01); *B01J 35/1042* (2013.01); *B01J 37/084* (2013.01); *B01J 37/0018* (2013.01); *B01J 21/04* (2013.01); *B01J 35/1009* (2013.01); *B01J 37/06* (2013.01); *B01J 37/0201* (2013.01); *B01J 35/1038* (2013.01); *B01J 35/026* (2013.01); *B01J 35/002* (2013.01)
USPC ............ 502/415; 502/100; 502/400; 502/414

(58) Field of Classification Search
USPC .................................. 502/415, 100, 400, 414
See application file for complete search history.

(56) References Cited

U.S. PATENT DOCUMENTS

| | | | |
|---|---|---|---|
| 4,039,561 A | 8/1977 | Mitsuhata et al. | |
| 4,125,480 A | 11/1978 | Maxwell | |
| 4,186,106 A | 1/1980 | Rebsdat et al. | |
| 4,207,210 A * | 6/1980 | Kilty ............................ | 502/348 |
| 4,242,235 A | 12/1980 | Cognion et al. | |
| 4,305,844 A | 12/1981 | Vangermain et al. | |
| 4,366,092 A | 12/1982 | Winterton | |
| 4,761,394 A | 8/1988 | Lauritzen | |
| 4,766,105 A * | 8/1988 | Lauritzen ...................... | 502/216 |
| 4,786,743 A | 11/1988 | Bongaarts et al. | |
| 4,797,270 A | 1/1989 | Alvarado Cendan et al. | |
| 4,810,689 A | 3/1989 | Hayden | |
| 5,063,195 A * | 11/1991 | Jin et al. ........................ | 502/341 |
| 5,077,256 A | 12/1991 | Yamamoto et al. | |
| 6,103,916 A * | 8/2000 | Takada et al. ................. | 549/534 |
| 6,846,774 B2 | 1/2005 | Rizkalla | |

FOREIGN PATENT DOCUMENTS

| | | |
|---|---|---|
| CN | 1044416 A | 8/1990 |
| CN | 1009437 B | 9/1990 |
| CN | 1467022 A | 1/2004 |
| CN | 1802211 A | 7/2006 |
| CN | 101007287 A | 8/2007 |
| CN | 101850243 A | 10/2010 |
| EP | 0211521 B1 | 3/1990 |
| JP | 56-164014 | 12/1981 |
| JP | 62-83041 A | 4/1987 |
| WO | WO 00/15333 | 3/2000 |
| WO | WO 00/15335 | 3/2000 |
| WO | WO 2007/085206 A1 | 8/2007 |

* cited by examiner

*Primary Examiner* — James McDonough
(74) *Attorney, Agent, or Firm* — Finnegan, Henderson, Farabow, Garrett & Dunner, LLP

(57) ABSTRACT

An alumina support comprises alpha-alumina as the main crystal phase of its backbone, and having a specific surface area of no higher than 3.0 m²/g, a pore volume ranging from 0.3 ml/g to 0.8 ml/g, an alkaline earth metal content ranging from 0.05% to 2.0% by weight of the support, wherein the support has such properties that treating the support with an aqueous oxalic acid solution having a concentration ranging from 0.4% to 2.0% by weight and having twice the weight of the support for 30 minutes can produce a leach liquor having an aluminum content of no higher than 60 µg/mL, a sodium content of no higher than 20 µg/mL, and a silicon content of no higher than 40 µg/mL. Processes for preparing the alumina support, silver catalysts comprising the alumina support, and methods of preparing ethylene oxide by ethylene oxidation using the silver catalyst are also disclosed herein.

13 Claims, No Drawings

ALUMINA SUPPORT, A PROCESS FOR PREPARING THE SUPPORT, A SILVER CATALYST PREPARED FROM THE SUPPORT, AND USE THEREOF

This application claims priority under 35 U.S.C. §119 to Chinese Patent Application No. 201010534019.6, filed Nov. 2, 2010.

The present disclosure relates to alumina supports, processes for preparing the alumina support, silver catalysts prepared from the alumina support, and methods for producing ethylene oxide using the silver catalyst.

By using molecular oxygen as an oxidant, alkenes can be directly oxidized to alkene oxides. The oxidation reaction can be conducted in the presence of silver deposited on an inert support as a catalyst. The support of the catalyst is usually deposited with other components as promoters. The inert support may be a porous solid such as alpha-alumina.

It is an important catalytic reaction process that ethylene reacts with oxygen over a silver catalyst to form ethylene oxide. In the production of ethylene oxide by ethylene oxidation, using a silver catalyst with high activity, selectivity and stability can greatly improve the economical benefits. Therefore, further improved silver catalysts are still sought.

The performance of the silver catalyst can be influenced by not only the composition and the preparation process of the catalyst, but also the properties and the preparation process of the support used in the catalyst.

Both alkali metal and alkaline earth metal are common promoters for the silver catalyst, as described in, for example, U.S. Pat. Nos. 4,039,561, 4,207,210, 4,305,844, 4,761,394, and 4,766,105.

In the silver catalyst for alkene oxidation, a support with alpha-alumina as the main component can be used. A suitable support can be selected to have a proper strength, a specific area and a pore-structure providing enough space for the oxidation of alkenes and dispersion of the reaction heat. A suitable support can also facilitate the timely desorption of the reaction product, alkene oxides, to prevent deep oxidation of the reaction product into side products such as carbon dioxide. The impurities introduced by the starting material, due to uncertainty of their identities and amounts, can result in fluctuations of the activity, selectivity and stability of the catalyst. In one embodiment, therefore, the surface of the alumina support is as pure as possible.

The surface of the support can be modified to enhance the catalytic performance of the silver catalyst through treating the prepared catalyst to improve the dispersion of the catalytically active component silver, change the degree of acidity or basicity on the surface of the support, and adjust the electronic states of the metal silver on the surface and the adsorption and desorption of reaction substances on the metal silver. In this aspect, some work has been reported, for example, in U.S. Pat. Nos. 4,797,270, 4,810,689, 4,186,106, 4,125,480, 4,366,092, 6,103,916 and 4,786,743, Chinese Patent Nos. CN1467022A and CN1044416A, Japanese Patent No. JP56164014, European Patent No. EP211521, and PCT Publication Nos. WO0015333 and WO0015335.

Nevertheless, there is still a need to improve the performance of the silver catalyst in the production of ethylene oxide by ethylene oxidation by enhancing its activity, selectivity and stability, to reduce ethylene consumption in the production of ethylene oxide.

The present inventors have surprisingly found that when a shaped and semi-finished alpha-alumina support comprising at least one alkaline earth metal is treated with at least one thermally decomposable organic acid solution having a pH of no more than 2.5 (such as an aqueous solution) and then heat-treated to produce an alpha-alumina support, the catalyst obtained by loading at least one silver active component onto the thus prepared alpha-alumina support has shown an excellent catalytic activity and/or selectivity in the production of ethylene oxide by ethylene oxidation.

Disclosed herein is an alumina support for silver catalysts used in production of ethylene oxide.

The alumina support disclosed herein comprises alpha-alumina as the main crystal phase of its backbone, wherein the alumina support has, for example, a specific surface area of no higher than 3.0 $m^2/g$, such as ranging from 0.5 $m^2/g$ to 2.0 $m^2/g$, a pore volume ranging from 0.3 ml/g to 0.8 ml/g, such as from 0.4 ml/g to 0.7 ml/g, and an alkaline earth metal content ranging from 0.05% to 2.0%, such as from 0.1% to 1.0%, by weight relative to the total weight of the support. The support disclosed herein has such properties that treating the support with an aqueous oxalic acid solution having a concentration ranging from 0.4% to 2.0% by weight and having twice the weight of the support for 30 minutes can produce a leach liquor having an aluminum content of no higher than 60 µg/mL, such as no higher than 30 µg/mL, a sodium content of no higher than 20 µg/mL, such as no higher than 10 µg/mL, and a silicon content of no higher than 40 µg/mL, such as no higher than 20 µg/mL.

Further disclosed herein is a process for preparing the alumina support, comprising:

(a) mixing at least one alumina starting material, at least one alkaline earth metal salt, optionally at least one carbonaceous burnout material, optionally at least one fluoride, at least one binder and water to produce a mixture, wherein the alumina starting material comprises alpha-alumina trihydrate and pseudo-boehmite in a weight ratio of alpha-alumina trihydrate to pseudo-boehmite ranging from 0.5:1 to 5:1, such as from 1:1 to 4:1, and wherein:

the amount of the alkaline earth metal salt, calculated based on the alkaline earth metal atom, ranges from 0.05% to 3.0% by weight relative to the total weight of the alumina starting material, the amount of the carbonaceous burnout material ranges from 0 to 30% by weight relative to the total weight of the alumina starting material, the amount of the fluoride ranges from 0 to 3% by weight relative to the total weight of the alumina starting material, and the total amount of the binder and water ranges from 10% to 40% by weight relative to the total weight of the alumina starting material;

(b) extruding the mixture obtained in step (a) to obtain shaped entities;

(c) drying the shaped entities obtained in step (b) at a temperature ranging from 60° C. to 200° C.;

(d) calcining the shaped entities obtained in step (c) at a temperature ranging from 1100° C. to 1600° C. to convert to a semi-finished alpha-alumina support;

(e) treating the semi-finished alpha-alumina support obtained in step (d) with a thermally decomposable organic acid solution having a pH of no higher than 2.5 (such as an aqueous solution);

(f) washing the treated support obtained in step (e) with water to produce a leach liquor having a pH of higher than 5 and a water-washed product; and (g) heat-treating the water-washed product obtained in step (f) at a temperature ranging from 80° C. to 1200° C., such as from 260° C. to 1200° C. and further such as from 1000° C. to 1200° C.

In some embodiments, the thermally decomposable organic acid solution used in step (e) of the process disclosed herein is substantially free of fluorine. The thermally-decomposable organic acid solution may, for example, be used in such an amount that the semi-finished alpha-alumina support can be fully immersed therein. In some embodiments, the solution comprises at least one thermally-decomposable organic acid chosen from formic acid, acetic acid, propionic acid, butyric acid, oxalic acid, benzoic acid, and phenol. In some embodiments, the at least one thermally-decomposable organic acid is chosen from formic acid, acetic acid, and oxalic acid.

According to the process disclosed herein, the at least one carbonaceous burnout material may be chosen, for example, from petroleum coke, carbon powder, graphite, polyethylene, polypropylene, rosin, and vaseline.

The at least one alkaline earth metal salt may be chosen, for example, from salts of barium, magnesium, calcium and/or strontium, such as chloride, sulfate, nitrate, phosphate and/or oxalate thereof. In some embodiments, the alkaline earth metal salt is barium sulfate. In some other embodiments, the alkaline earth metal salt is magnesium nitrate.

The at least one fluoride may be chosen, for example, from aluminum fluoride and ammonium fluoride.

The at least one binder may be chosen, for example, from nitric acid and acetic acid.

In some embodiments of the process disclosed herein, a portion or all of the alpha-alumina trihydrate can be replaced by a substituting alumina powder which has been pre-calcined into alpha-alumina or a transition alumina; a portion or all of the pseudo-boehmite can be replaced by an alumina sol; the ratio of the total weight of alpha-alumina trihydrate and its substitute if present to the total weight of pseudo-boehmite and its substitute if present may range, for example, from 0.5:1 to 5:1, such as from 1:1 to 4:1.

Further disclosed is a silver catalyst for producing ethylene oxide from ethylene by gas-phase catalytic oxidation, comprising:
 the alumina support disclosed herein or the alumina support prepared by the process disclosed herein;
 silver deposited thereon in an amount, calculated based on the silver atom, ranging from 1% to 45% by weight relative to the total weight of the silver catalyst;
 at least one alkali metal promoter in an amount, calculated based on the alkali metal atom, ranging from 10 ppm to 2000 ppm by weight relative to the total weight of the silver catalyst;
 at least one rhenium promoter in an amount, calculated based on the rhenium atom, ranging from 10 ppm to 2000 ppm by weight relative to the total weight of the silver catalyst;
 at least one optional alkaline earth metal promoter; and
 at least one optional co-promoter of the rhenium promoter.

In the silver catalyst disclosed herein, the at least one alkali metal promoter comprises at least one element chosen, for example, from Li, Na, K, Rb and Cs.

The at least one alkaline earth metal promoter comprises at least one element chosen, for example, from Mg, Ca, Sr and Ba.

The at least one co-promoter of the rhenium promoter comprises at least one element chosen, for example, from cerium, sulfur, molybdenum, tungsten, chromium, and manganese.

Even further disclosed herein is a method for producing ethylene oxide by ethylene oxidation using the silver catalyst disclosed herein.

Generally, the process for preparing the alumina support disclosed herein comprises: preparing a semi-finished alpha-alumina support comprising at least one alkaline earth metal, treating the support with a thermally decomposable organic acid solution, and then heating the treated support to obtain the finished alumina support.

The process for preparing the semi-finished alpha-alumina support comprising at least one alkaline earth metal is well known by those skilled in the art and disclosed in, for example, Chinese Patent Nos. CN101007287A and CN1009437B.

To prepare the alumina support disclosed herein, an alumina starting material comprising alpha-alumina trihydrate and pseudo-boehmite can be used. In some embodiments, the alumina starting material comprises alpha-alumina trihydrate and pseudo-boehmite. In some embodiments, the alumina starting material consists essentially of alpha-alumina trihydrate and pseudo-boehmite. In some embodiments, the alumina starting material consists of alpha-alumina trihydrate and pseudo-boehmite. In the alumina starting material, the weight ratio of alpha-alumina trihydrate to pseudo-boehmite can range, for example, from 0.5:1 to 5:1, such as from 1:1 to 4:1. In some embodiments, the contents of Na and Si in the alpha-alumina trihydrate and the pseudo-boehmite in the alumina starting material may, for example, be less than 0.2% by weight, relative to the weight of the alpha-alumina trihydrate and the weight of the pseudo-boehmite, respectively. In the process of preparing the semi-finished alpha-alumina support disclosed herein, a portion or all of the alpha-alumina trihydrate can be replaced by a substituting alumina powder, which has been pre-calcined into alpha-alumina or a transition alumina; a portion or all of the pseudo-boehmite can be replaced by an alumina sol; the ratio of the total weight of alpha-alumina trihydrate and its substitute if present to the total weight of pseudo-boehmite and its substitute if present may range, for example, from 0.5:1 to 5:1, such as from 1:1 to 4:1.

In preparing the semi-finished alpha-alumina support disclosed herein, at least one alkaline earth metal salt can be used. Thus, in some embodiments, the semi-finished alpha-alumina support comprises at least one alkaline earth metal. The alkaline earth metal salt may be chosen, for example, from salts of barium, magnesium, calcium and/or strontium, including organic and inorganic salts thereof, such as chloride, sulfate, nitrate, phosphate, and oxalate thereof. In some embodiments, the alkaline earth metal salt may be chosen from chloride, sulfate and nitrate of magnesium and/or barium. In an embodiment, barium sulfate and/or magnesium nitrate may be used. In some embodiments, the alkaline earth metal salt is added in an amount, calculated based on the alkaline earth metal atom, ranging from 0.05% to 3.0%, such as from 0.1% to 2.5% and further such as from 0.2% to 2.0%, by weight relative to the total weight of the alumina starting material.

In the preparation of the semi-finished alpha-alumina support disclosed herein, the at least one carbonaceous burnout material is added to form large pores and provide the support with a suitable pore structure and specific surface area.

In some embodiments, the at least one carbonaceous burnout material may be chosen from petroleum coke, carbon powder, graphite, polyethylene, polypropylene, rosin, and vaseline. In some embodiments, the at least one carbonaceous burnout material may be chosen from petroleum coke, graphite, and vaseline. The at least one carbonaceous burnout material is oxidized during the calcining procedure with gas being formed and released to form large pores in the support. In some embodiments, the at least one carbonaceous burnout material is added in an amount ranging from 0 to 30% by weight, such as from 0.01% to 20%, further such as from 0.1% to 10%, and even further such as from 0.1% to 6% by weight relative to the total weight of the alumina starting material.

In the preparation of the semi-finished alpha-alumina support disclosed herein, the at least one fluoride may be chosen, for example, from hydrogen fluoride, ammonium fluoride, aluminum fluoride, magnesium fluoride, and cryolite. In some embodiments, the at least one fluoride is chosen from aluminum fluoride and ammonium fluoride. The role of the at least one fluoride is to accelerate the conversion of the alumina crystalline form and reduce the amount of micropores having a size of 0.1 μm or less. In some embodiments, the at least one fluoride is added in an amount ranging from 0 to 3% by weight, such as from 0.1% to 2%, further such as from 0.3% to 1.8%, and even further such as from 0.5% to 1.8% by weight relative to the total weight of the alumina starting material.

In the preparation of the semi-finished alpha-alumina support disclosed herein, at least one binder can be added. The binder and the pseudo-boehmite in the alumina starting material may form an alumina sol, which bind components together to form a shaped paste after extruding. The binder comprises, for example, acids, such as nitric acid, formic acid, acetic acid, propionic acid and/or hydrochloric acid. In an embodiment, the binder may comprise nitric acid and/or acetic acid. In some embodiments, an aqueous nitric acid solution can be used as the binder, wherein the weight ratio of nitric acid to water ranges, for example, from 1:1.25 to 1:10, such as from 1:2 to 1:6.

There is no particular limitation on the amount of the binder used herein, provided that the binder is in an amount sufficient to bind components together. In some embodiments, the binder is used in an amount ranging from 2% to 10% by weight, such as from 3% to 8% by weight relative to the total weight of the alumina starting material. In some embodiments, the binder and water are in a total amount ranging from 15% to 30% by weight, such as from 20% to 30% by weight relative to the total weight of the alumina starting material. In some embodiments, the weight ratio of the binder to water ranges from 1:0.5 to 1:14, such as from 1:1.5 to 1:9.

In the preparation of the semi-finished alpha-alumina support disclosed herein, a portion or all of the pseudo-boehmite can be replaced by an alumina sol. In some embodiment when all of the pseudo-boehmite is replaced by the alumina sol, no binder is added in step (a) of the process disclosed herein, and water is added in an amount ranging from 15% to 30% by weight, such as 20% to 30% by weight, relative to the total weight of the alumina starting material. In some embodiments when a portion of the pseudo-boehmite is replaced by the alumina sol, a suitable amount of the binder is added to bind components together. For example, the total weight of the binder and water may range from 15% to 30%, such as from 20% to 30%, by weight relative to the total weight of the alumina starting material; and the weight ratio of the binder to water may range, for example, from 1:0.5 to 1:14, such as from 1:1.5 to 1:9.

After mixing the components in step (a) of the process disclosed herein, a paste may be obtained. Then the paste is extruded to form shaped entities. The shaped entities can be dried to have a moisture content of, for example, 10% by weight or less. The drying temperature can range, for example, from 60° C. to 200° C. The drying period of time can be adjusted depending on the moisture content, for example, ranging from 1 hour to 24 hours. The shaped entities thus obtained can be in a form of ring, sphere, column or multihole column.

The dried shaped entities may be calcined at a temperature ranging, for example, from 1100° C. to 1600° C., such as from 1200° C. to 1500° C., for a period of time ranging, for example, from 2 hours to 20 hours. Substantially all of the alumina, for example, more than 90% by weight of the alumina, can be converted to alpha-alumina by the calcination to produce the semi-finished alpha-alumina support.

The semi-finished alpha-alumina support thus obtained may be treated with a thermally decomposable organic acid solution having a pH of no higher than 2.5 in step (e) of the process disclosed herein. According to the present disclosure, the pH is measured at about 25° C. In some embodiments, the thermally decomposable organic acid solution has a pH ranging from 0.4 to 2.5, such as from 0.6 to 2.5, further such as from 0.4 to 2.0, even further such as from 0.6 to 2.0. In some embodiments, the thermally decomposable organic acid solution has a pH ranging from 0.4 to 0.75, such as from 0.6 to 0.75.

The at least one thermally decomposable organic acid will not remain after the heat treatment in step (g) of the process disclosed herein, and thus it will not have a negative effect on the performance of the catalyst made from the support disclosed herein. In some embodiments, the at least one thermally-decomposable organic acid is chosen from formic acid, acetic acid, propionic acid, butyric acid, oxalic acid, benzoic acid, and phenol. In some embodiments, the at least one thermally decomposable organic acid is chosen from formic acid, acetic acid, and oxalic acid. In an embodiment, the at least one thermally decomposable organic acid is formic acid. In another embodiment, the at least one thermally decomposable organic acid is acetic acid. In yet another embodiment, the thermally-decomposable organic acid is oxalic acid. The thermally-decomposable organic acid can be formulated in a suitable solvent such as water, alcohol and/or ether. In an embodiment, the solvent is water. For easy operation and safety consideration, an aqueous oxalic acid solution can be used; for example, an aqueous oxalic acid solution formulated with solid oxalic acid can be used. In some embodiments, the thermally decomposable organic acid solution is substantially free of fluorine, wherein the phrase "thermally-decomposable organic acid solution is substantially free of fluorine" means that the thermally decomposable organic acid solution has a fluorine content, calculated based on the fluorine atom, of less than 0.1%, such as less than 0.05% and further such as less than 0.001%, by weight of the solution. In an embodiment, the thermally decomposable organic acid solution is free of fluorine.

In step (e) of the process disclosed herein, a thermally decomposable organic acid solution having a pH of no higher than 2.5 is used to treat the semi-finished alpha-alumina support. If the pH is too high, the silica and alumina on the support's surface may not be well washed off. The inorganic acid is easy to form a less soluble salt with the alkaline earth metal on the support's surface, thus introducing new impurities and affecting the performance of the catalyst. The thermally decomposable organic acid solution having a pH of no more than 2.5 may be used in such an amount that the semi-finished alpha-alumina support can be fully immersed therein. In some embodiments, the thermally decomposable organic acid solution having a pH of no higher than 2.5 is used in an amount that is at least 1.6 times, such as from 1.6 times to 3 times, the weight of the semi-finished alpha-alumina support.

As disclosed herein, using the thermally-decomposable organic acid solution having a pH of no higher than 2.5 to treat the semi-finished alpha-alumina support means that the semi-finished alpha-alumina support is subjected to the operation such as impregnating, suspending and the like. This treatment may, for example, be conducted for at least 10 minutes, such as from 10 minutes to 600 minutes, and at a temperature ranging, for example, from 0° C. to 90° C.

In the process for preparing the alumina support disclosed herein, for the purpose of decreasing the content of impurities such as Na and Si on the support surface, the support can be washed with distilled water or deionized water, such as with excessive distilled water or deionized water, for 1-5 times after the step (e); and then the heat-treatment of the step (f) is continued. In the process for preparing the alumina support disclosed herein, in the step (f), the support treated in the step (e) can be washed with distilled water or deionized water, e.g. excessive distilled water or deionized water, for example for 4-6 times, until a leach liquor having a pH of higher than 5 can be obtained. The support after the water-washing may be substantially free of organic acid salts.

In step (g) of the process for preparing the alumina support disclosed herein, the water-washed product obtained in the step (f) is subjected to a heat-treatment at a temperature ranging, for example, from 80° C. to 1200° C. for a period ranging, for example, from 5 minutes to 600 minutes, to produce a finished alumina support. The heat-treatment may comprise drying and calcination. In some embodiments, the drying treatment is conducted at a temperature ranging from 80° C. to 400° C., and the calcination is conducted at a temperature ranging from 400° C. to 1200° C. In some embodiments, the water-washed product obtained in step (f) is heat-treated in step (g) at a temperature ranging from 260° C. to 1200° C., such as from 1000° C. to 1200° C. Step (g) can be conducted in a flowing atmosphere. In an embodiment, the step (g) is conducted in a flowing atmosphere having a moisture content of less than 1% by weight. In an embodiment, step (g) is conducted in air or in an inert atmosphere. After step (g), the alpha-alumina support disclosed herein can be obtained.

Further disclosed herein is an alumina support, comprising alpha-alumina as the main crystal phase of its backbone. The alumina support disclosed herein has such properties that treating the alumina support with an aqueous oxalic acid solution having a concentration ranging from 0.4% to 2.0% by weight, such as 0.6% by weight, and having twice the weight of the support for 30 minutes can produce a leach liquor having an aluminum content of no higher than 60 µg/mL, such as no higher than 30 µg/mL. The leach liquor can also have a sodium content of no higher than 20 µg/mL, such as no higher than 10 µg/mL. The leach liquor can further have a silicon content of no higher than 40 µg/mL, such as no higher than 20 µg/mL. In an embodiment, the alumina support disclosed herein may have a specific surface area of no higher than 3.0 m$^2$/g, such as ranging from 0.5 m$^2$/g to 2.0 m$^2$/g. The alumina support disclosed herein may also have a pore volume ranging, for example, from 0.3 ml/g to 0.8 ml/g, such as from 0.4 ml/g to 0.7 ml/g. The alumina support disclosed herein may still have an alkaline earth metal content ranging, for example, from 0.05% to 2.0%, such as from 0.1% to 1.0%, by weight relative to the total weight of the support.

The alumina support described above can be prepared by the process disclosed herein for preparing the alumina support. Further disclosed herein is an alumina support prepared by the process disclosed herein for preparing the alumina support.

As disclosed herein, the specific surface area of the support is measured according to the International Standard ISO-9277 by the Nitrogen Gas Physical Adsorption BET Method. For example, the specific surface area of the support can be measured with Nitrogen Gas Physical Adsorption Instrument NOVA2000e (Quantachrome Corp., USA).

The pore volume of the support is measured by the mercury porosimetry. For example, the pore volume of the support can be measured with AutoPore9510-type Mercury Porosimeter (Micromeritics Instrument Corp., USA).

The alkaline-earth metal content in the support can be obtained by calculation or measurement (for example, X-Ray fluorescence).

The radial crush strength of the support can be measured with the DL II type Particle Strength Tester (manufactured by Dalian Research and Design Institute of Chemical Industry) by, for example, randomly selecting thirty support sample particles, measuring the radial crush strength for each particle, and then calculating an average radial crush strength.

The water absorption of the support means the volume of water that is absorbed in saturation by a unit mass of the support and is expressed as mL/g. The water absorption can be determined by weighing a certain amount of the support (assuming its mass as $m_1$), boiling the support in boiling water for 1 hour, removing the support from boiling water, keeping the support upright on a wet gauze having a suitable water content to remove the redundant water from the support, finally weighing the water-absorbing support (assuming its mass as $m_2$), and calculating the water absorption according to the following formula:

$$\text{Water absorption}=(m_2-m_1)/m_1/\rho_{water},$$

wherein $\rho_{water}$ is the water density at the measuring temperature under atmospheric pressure.

The alumina support disclosed herein can be in any form known in the art, such as ring, sphere, column or multihole column. In some embodiments, the alpha-alumina support can be in a form of multi-hole honeycomb-like cylindrical particles with an outer diameter ranging, for example, from 5 mm to 9 mm and a small hole diameter ranging, for example, from 1 mm to 2 mm. In some embodiments, the alumina support can be in a form of single-hole circular ring-like particles with an outer diameter ranging, for example, from 5 mm to 9 mm and an inner diameter ranging, for example, from 2 mm to 5 mm.

The silver catalyst disclosed herein can be prepared using the alumina support set forth above. The silver catalyst disclosed herein can be produced in a conventional manner, for example, by impregnating the alumina support set forth above with a solution comprising at least one silver compound, at least one organic amine, at least one alkali metal promoter and at least one rhenium promoter.

The process for preparing the silver catalyst disclosed herein comprises:

(1) impregnating the alumina support disclosed herein with a solution comprising sufficient amount of at least one silver compound, at least one organic amine, at least one alkali metal promoter, at least one rhenium promoter, at least one optional alkaline earth metal promoter and at least one optional co-promoter of the rhenium promoter;

(2) filtering the impregnation solution;

(3) activating the support obtained in step (2) in air or an inert gas to produce the silver catalyst; and optionally (4) repeating steps (1), (2) and (3), to produce the silver catalyst.

The silver compound can be any silver compound suitable for preparing the silver catalyst for the production of ethylene oxide. As disclosed herein, the at least one silver compound can be chosen, for example, from silver oxide, silver nitrate and silver oxalate. The amount of the silver compound used in the impregnation procedure may be sufficient so that silver in the finally produced silver catalyst can be in an amount ranging, for example, from 1% to 45% by weight, such as from 5% to 40%, further such as from 8% to 35%, and even further such as from 15% to 25%, by weight, calculated based on the silver atom, relative to the total weight of the catalyst.

The at least one organic amine can be any organic amine compound suitable for preparing the silver catalyst for the production of ethylene oxide, provided that the organic amine compound has an ability to form a silver-amine complex with the silver compound. As disclosed herein, the at least one organic amine can be chosen, for example, from pyridine, butyl amine, ethylene diamine, 1,3-propylene diamine, and ethanolamine. In some embodiments, a mixture of ethylene diamine and ethanolamine can be used.

In the process for preparing the silver catalyst disclosed herein, the at least one alkali metal promoter can be chosen, for example, from a lithium compound, a sodium compound, a potassium compound, a rubidium compound and a cesium compound, such as nitrate, sulfate and hydroxide thereof. In some embodiments, the at least one alkali metal promoter is chosen from a lithium compound, a potassium compound and a cesium compound, such as cesium sulfate, cesium nitrate, lithium nitrate, lithium sulfate and potassium hydroxide. In some embodiments, the at least one alkali metal promoter may be added to the impregnation solution in such an amount that the alkali metal may be present in the final silver catalyst in an amount ranging, for example, from 10 ppm to 2000 ppm by weight, such as from 50 ppm to 2000 ppm and from 50 ppm to 1500 ppm by weight, calculated based on the alkali metal atom, relative to the total weight of the catalyst.

In the process for preparing the silver catalyst disclosed herein, the at least one rhenium promoter can be chosen, for example, from rhenium oxide, perrhenic acid, and perrhenate. In some embodiments, the at least one rhenium promoter is chosen from perrhenic acid and perrhenate, such as perrhenic acid, cesium perrhenate, and ammonium perrhenate. The at least one rhenium promoter may be added to the impregnation solution in such an amount that the rhenium metal may be present in the final silver catalyst in an amount ranging, for example, from 10 ppm to 2000 ppm by weight, such as from 100 ppm to 1000 ppm by weight, calculated based on the rhenium metal atom, relative to the total weight of the catalyst.

In the process for preparing the silver catalyst disclosed herein, the at least one optional alkaline earth metal promoter can be chosen, for example from a magnesium compound, a calcium compound, a strontium compound and a barium compound, such as oxide, oxalate, sulfate, acetate and nitrate thereof. In some embodiments, the at least one optional alkaline earth metal promoter can be chosen from a barium compound and a strontium compound, such as barium acetate and strontium acetate. The at least one optional alkaline earth metal promoter may be added to the impregnation solution in such an amount that the content of the alkaline-earth metal in the final silver catalyst ranges from 400 ppm to 17000 ppm by weight, such as from 400 ppm to 10000 ppm by weight, calculated based on the alkaline-earth metal atom, relative to the total weight of the catalyst.

The at least one optional co-promoter of the rhenium promoter can be also added to further improve the activity, selectivity and stability of the obtained silver catalyst. The co-promoter of the rhenium promoter disclosed herein can be a compound of any transition metal (such as cerium, molybdenum, tungsten, chromium, and manganese) in the Periodic Table, or a mixture of transitional metal compounds, such as an oxyacid of an element selected from Groups VIIB and VIIB, and a salt thereof. In some embodiments, tungstenic acid, ammonium tungstate, cesium tungstate, molybdic acid, ammonium molybdate or a tetrahydrate thereof, ammonium metatungstate, ceric sulfate tetrahydrate $(Ce(SO_4)_2 \cdot 4H_2O)$ and the like can be used. Sulfur can be also used as the at least one optional co-promoter of the rhenium promoter.

The at least one optional co-promoter of the rhenium promoter may be added in such an amount that the content of the co-promoter of the rhenium promoter in the final catalyst may range, for example, from 0 to 1000 ppm, such as from 0 to 800 ppm, calculated based on the weight of the active element (such as cerium, sulfur, molybdenum, tungsten, chromium, and manganese), relative to the total weight of the catalyst. The co-promoter of the rhenium promoter can be applied to the support before, during or after the silver impregnation, or impregnated onto the support after the silver compound has been reduced.

To load silver homogenously and thoroughly, a vacuum-pumping may be used before impregnating the alumina support, for example, to an absolute pressure below 10 mmHg. The impregnation with the impregnation solution may be conducted for a period ranging from 10 minutes to 60 minutes. After filtering, the support may be activated in a flowing atmosphere, e.g. in air or an inert gas such as nitrogen and argon, at a temperature ranging from 200° C. to 500° C. for more than 2 minutes, such as from 2 minutes to 120 minutes and further such as from 2 minutes to 60 minutes. To ensure that the catalyst has a relative high activity, the activation may be conducted at a temperature of no higher than 500° C.

In an embodiment for preparing the silver catalyst disclosed herein, an aqueous solution of silver nitrate is first treated with an aqueous solution of ammonium oxalate or oxalic acid to produce a precipitate of silver oxalate. The precipitate of silver oxalate is filtered, washed with deionized water until no nitrate ion is present, and dried. The silver oxalate is then dissolved into an aqueous solution of at least one organic amine chosen, for example, from pyridine, butyl amine, ethylene diamine, 1,3-propylene diamine, and ethanolamine. Promoters are added to formulate an impregnation solution. Then the alumina support is impregnated with the obtained impregnation solution under an absolute pressure below 10 mmHg for a period of time ranging from 10 minutes to 60 minutes, dried, and kept in air or in an inert atmosphere at a temperature ranging from 200° C. to 500° C. for a period of time ranging from 2 minutes to 120 minutes, such as from 2 minutes to 60 minutes, for activation. Alternatively, the silver nitrate used herein can be replaced with silver oxide; and the silver oxalate obtained can also not be subjected to the filtration, but directly form a complex with the at least one organic amine, followed by the impregnation of the support.

The silver catalyst obtained by the process disclosed herein can be used in a gas-solid phase catalytic oxidation of ethylene to produce ethylene oxide.

Further disclosed herein is a silver catalyst prepared according to the process set forth above and useful in a gas-phase catalytic oxidation of ethylene to produce ethylene oxide, wherein the silver catalyst comprises:
   the alumina support disclosed herein,
   silver deposited thereon in an amount, calculated based on the silver atom, ranging from 1% to 45% by weight relative to the total weight of the silver catalyst, at least one alkali metal promoter in an amount, calculated based on the alkali metal atom, ranging from 10 ppm to 2000 ppm by weight relative to the total weight of the silver catalyst, at least one rhenium promoter in an amount, calculated based on the rhenium atom, ranging from 10 ppm to 2000 ppm by weight relative to the total weight of the silver catalyst, at least one optional alkaline earth metal promoter, and at least one optional co-promoter of the rhenium promoter.

Even further disclosed herein is a method of using the silver catalyst disclosed herein in the production of ethylene oxide by ethylene oxidation.

EXAMPLES

The present disclosure is illustrated by the following non-limiting examples.

Catalyst Performance Evaluation

The silver catalysts used in the examples were tested in a laboratory micro-reactor for the catalytic performance and the stability. In the micro-reactor testing apparatus, the reactor was a stainless steel reaction tube having an inner diameter of 4 mm. The reaction tube was disposed in a heating jacket. The loading volume of the catalyst was 1 mL (the particle size of the catalyst ranged from 12 to 18 meshes). An inert filler was disposed in the lower portion so that the catalyst bed was located in an area of the heating jacket with constant temperature.

The standard evaluation conditions for evaluating the catalytic activity and the selectivity in the present disclosure were as follows (the actual reaction conditions are listed in the examples):

The composition of the reaction gas (mol %):

| | |
|---|---|
| Ethylene ($C_2H_4$) | 30.0 ± 2.5 |
| Oxygen ($O_2$) | 7.2 ± 0.5 |
| Carbon dioxide ($CO_2$) | <3.0 |
| Ballast gas($N_2$) | Balance |
| Inhibitor 1,2-dichloroethane | 0.3-2.0 ppmv |
| Reaction pressure | 1.8 MPa |
| Space velocity | 4500-7000 $h^{-1}$ |
| The concentration of ethylene oxide (EO) in the effluent from the reactor | 1.8-2.5% |

Under a certain space velocity, when the reaction became stable and reached the above reaction conditions, the compositions of the gases at the inlet and the outlet of the reactor were continually measured. The measurement results, after the volume-shrinkage correction, were used to calculate the selectivity according to the following formula:

$$S = \frac{\Delta EO}{\Delta EO + 0.5 \times \Delta CO_2} \times 100\%$$

wherein $\Delta EO$ is the difference between the ethylene oxide concentrations at the outlet and the inlet of the reactor; and $\Delta CO_2$ is the difference of the carbon dioxide concentrations at the outlet and the inlet of the reactor. Ten or more sets of experiment data were recorded and averaged as the experiment result of that day.

Preparation for the Support

Support 1.1

312 g of alpha-alumina trihydrate (50-500 meshes), 92 g of pseudo-boehmite (≤200 meshes), 5 g of petroleum coke, 7 g of $NH_4F$ and 8.5 g of $Mg(NO_3)_2$ were placed into a mixer to mix homogenously, transferred into a kneader, then 0.12 L of a diluted nitric acid aqueous solution (nitric acid:water=1:3 by weight) was added, kneaded to an extrudable paste, and extruded to form five-hole cylinder entities with an outer diameter of 8.0 mm, a length of 6.0 mm and an inner diameter of 1.0 mm. The cylinder entities were dried at a temperature ranging from 80° C. to 120° C. for 2 hours, and the free water content was decreased to below 10% by weight. The dried cylinder entities were placed in a top-hat kiln and heated for 30 hours from room temperature (about 25° C.) to 1410° C., and kept at 1410° C. constantly for 2 hours to obtain a white alpha-alumina Support 1.1.

Support 1.1 had a shape of five-hole cylinder with an outer diameter of 8.0 mm, a length of 6.0 mm and an inner diameter of 1.0 mm, a specific surface area of 0.99 $m^2$/g, a water adsorption of 50.1% by weight, a pore volume of 0.60 ml/g, a radial crush strength of 78 N/particle, and an alkaline earth metal magnesium content of 0.49% by weight.

Support 1.2

212 g of alpha-alumina trihydrate (50-500 meshes), 192 g of pseudo-boehmite (≤200 meshes), 4 g of finely-ground barium sulfate and 7 g of $NH_4F$ were placed into a mixer to mix homogenously, transferred into a kneader, then 4 g of vaseline and 0.12 L of a diluted nitric acid aqueous solution (nitric acid:water=1:3 by weight) were added, kneaded to an extrudable paste, and extruded to form five-hole cylinder entities with an outer diameter of 8.0 mm, a length of 6.0 mm and an inner diameter of 1.0 mm. The cylinder entities were dried at a temperature ranging from 80° C. to 120° C. for 5 hours, and the free water content was decreased to below 10% by weight. The dried cylinder entities were placed in a top-hat kiln and heated for 30 hours from room temperature (about 25° C.) to 1230° C., and kept at 1230° C. constantly for 10 hours to obtain a white alpha-alumina Support 1.2.

Support 1.2 had a shape of five-hole cylinder with an outer diameter of 8.0 mm, a length of 6.0 mm and an inner diameter of 1.0 mm, a specific surface area of 1.45 $m^2$/g, a water adsorption of 53.7% by weight, a pore volume of 0.62 ml/g, a radial crush strength of 90 N/particle, and an alkaline earth metal barium content of 0.78% by weight.

Support 1.3

242 g of alpha-alumina trihydrate (50-500 meshes), 162 g of pseudo-boehmite (≤200 meshes), 2 g of finely-ground barium sulfate and 7 g of $NH_4F$ were placed into a mixer to mix homogenously, transferred into a kneader, then 2 g of vaseline and 0.12 L of a diluted nitric acid aqueous solution (nitric acid:water=1:3 by weight) were added, kneaded to an extrudable paste, and extruded to form five-hole cylinder entities with an outer diameter of 8.0 mm, a length of 6.0 mm and an inner diameter of 1.0 mm. The cylinder entities were dried at a temperature ranging from 80° C. to 120° C. for 8 hours, and the free water content was decreased to below 10% by weight. The dried cylinder entities were placed in a top-hat kiln and heated for 30 hours from room temperature (about 25° C.) to 1300° C., and kept at 1300° C. constantly for 6 hours to obtain a white alpha-alumina Support 1.3.

Support 1.3 had a shape of five-hole cylinder with an outer diameter of 8.0 mm, a length of 6.0 mm and an inner diameter of 1.0 mm, a specific surface area of 1.34 $m^2$/g, a water adsorption of 53.1% by weight, a pore volume of 0.54 ml/g, a radial crush strength of 116 N/particle, and an alkaline earth metal barium content of 0.40% by weight.

Support 2.1

120 g of Support 1.1 was placed into an acid-resistant plastic container, into which was added 240 g of an aqueous oxalic acid solution with a pH of 0.75 at 25° C., soaked at room temperature for 40 minutes, filtered to remove the solution, then 150 g of distilled water was used to impregnate and wash the obtained sample for 20 minutes, and the sample was filtered to remove water. The washing was repeated thrice in the same manner to produce a leach liquor having a pH more than 5, and the sample was dried in a flowing air stream at 260° C. for 10 minutes to form Support 2.1.

Support 2.1 had a specific surface area of 0.98 m$^2$/g, a water adsorption of 50.8% by weight, a pore volume of 0.62 ml/g, a radial crush strength of 72 N/particle, and an alkaline earth metal magnesium content of 0.48% by weight.

Support 2.2

It was prepared in the same manner as in Support 2.1, except that after washing, the sample was dried in a flowing air stream at 400° C. for 5 minutes to form Support 2.2.

Support 2.2 had a specific surface area of 0.98 m$^2$/g, a water adsorption of 50.2% by weight, a pore volume of 0.60 ml/g, a radial crush strength of 74 N/particle, and an alkaline earth metal magnesium content of 0.48% by weight.

Support 2.3

It was prepared in the same manner as in Support 2.2, except that after drying, the sample was calcined in a muffle furnace at 500° C. for 5 hours to form Support 2.3.

Support 2.3 had a specific surface area of 0.95 m$^2$/g, a water adsorption of 51.2% by weight, a pore volume of 0.62 ml/g, a radial crush strength of 76 N/particle, and an alkaline earth metal magnesium content of 0.47% by weight.

Support 2.4

120 g of Support 1.2 was placed into an acid-resistant plastic container, into which was added 240 g of an aqueous oxalic acid solution with a pH of 0.75 at 25° C., soaked at room temperature for 40 minutes, filtered to remove the solution, then 150 g of distilled water was used to impregnate and wash the obtained sample for 20 minutes, and the sample was filtered to remove water. The washing was repeated in the same manner to produce a leach liquor having a pH more than 5, and the sample was heat-treated in a flowing air stream at 480° C. for 20 minutes to form Support 2.4.

Support 2.4 had a specific surface area of 1.46 m$^2$/g, a water adsorption of 53.8% by weight, a pore volume of 0.63 ml/g, a radial crush strength of 88 N/particle, and an alkaline earth metal barium content of 0.77% by weight.

Support 2.5

It was prepared in the same manner as in Support 2.4, except that after the heat-treatment, the sample was calcined in a muffle furnace at 700° C. for 5 hours to form Support 2.5.

Support 2.5 had a specific surface area of 1.49 m$^2$/g, a water adsorption of 54.1% by weight, a pore volume of 0.62 ml/g, a radial crush strength of 90 N/particle, and an alkaline earth metal barium content of 0.76% by weight.

Support 2.6

120 g of Support 1.2 was placed into an acid-resistant plastic container, into which was added 240 g of an aqueous oxalic acid solution with a pH of 2.4 at 25° C., soaked at 60° C. for 40 minutes, filtered to remove the solution, then 150 g of distilled water was used to impregnate and wash the obtained sample for 20 minutes, and the sample was filtered to remove water. The washing was repeated in the same manner to produce a leach liquor having a pH more than 5, and the sample was heat-treated in a flowing air stream at 480° C. for 20 minutes to form Support 2.6.

Support 2.6 had a specific surface area of 1.46 m$^2$/g, a water adsorption of 53.8% by weight, a pore volume of 0.62 ml/g, a radial crush strength of 90 N/particle, and an alkaline earth metal barium content of 0.76% by weight.

Support 2.7

120 g of Support 1.3 was placed into an acid-resistant plastic container, into which was added 240 g of an aqueous oxalic acid solution with a pH of 0.6 at 25° C., soaked at room temperature for 40 minutes, filtered to remove the solution, then 150 g of distilled water was used to impregnate and wash the obtained sample for 20 minutes, and the sample was filtered to remove water. The washing was repeated in the same manner to produce a leach liquor having a pH more than 5, and the sample was heat-treated in a flowing air stream at 500° C. for 20 minutes to form Support 2.7.

Support 2.7 had a specific surface area of 1.33 m$^2$/g, a water adsorption of 53.2% by weight, a pore volume of 0.55 ml/g, a radial crush strength of 109 N/particle, and an alkaline earth metal barium content of 0.39% by weight.

Support 2.8

120 g of Support 1.3 was placed into an acid-resistant plastic container, into which was added 240 g of an aqueous oxalic acid solution with a pH of 0.6 at 25° C., soaked at room temperature for 40 minutes, filtered to remove the solution, then 150 g of distilled water was used to impregnate and wash the obtained sample for 20 minutes, and the sample was filtered to remove water. The washing was repeated in the same manner to produce a leach liquor having a pH more than 5, and the sample was heat-treated in a flowing air stream at 90° C. for 500 minutes to form Support 2.8.

Support 2.8 had a specific surface area of 1.32 m$^2$/g, a water adsorption of 53.5% by weight, a pore volume of 0.54 ml/g, a radial crush strength of 113 N/particle, and an alkaline earth metal barium content of 0.39% by weight.

Support 2.9

Support 2.7 was further heated in a high-temperature top-hat kiln for 8 hours to 1000° C., kept at 1000° C. constantly for 3 hours, and naturally cooled down to obtain Support 2.9.

Support 2.9 had a specific surface area of 1.28 m$^2$/g, a water adsorption of 53.0% by weight, a pore volume of 0.53 ml/g, a radial crush strength of 129 N/particle, and an alkaline earth metal content of 0.38% by weight.

Support 3.1

100 g of Support 1.1 was placed into a vessel containing 200 g of distilled water, soaked for 40 minutes, filtered to remove the solution. The above treatment was repeated thrice in the same manner, the sample was dried in a flowing air stream at 300° C. for 10 minutes, and further calcined at 850° C. for 3 hours to form Support 3.1, which had the same physical properties as Support 1.1.

Support 3.2

120 g of Support 1.2 was placed into an acid-resistant plastic container, into which was added 240 g of an aqueous oxalic acid solution with a pH of 2.8 at 25° C., soaked at 60° C. for 40 minutes, filtered to remove the solution, then 150 g of distilled water was used to impregnate and wash the obtained sample for 20 minutes, and the sample was filtered to remove water. The washing was repeated in the same manner to produce a leach liquor having a pH more than 5, and the sample was heat-treated in a flowing air stream at 480° C. for 20 minutes to form Support 3.2.

Support 3.2 had a specific surface area of 1.47 m$^2$/g, a water adsorption of 53.5% by weight, a pore volume of 0.61 ml/g, a radial crush strength of 92 N/particle, and an alkaline earth metal barium content of 0.77% by weight.

Support 3.3

120 g of Support 1.3 was placed into an acid-resistant plastic container, into which was added 240 g of an aqueous hydrochloric acid solution with a pH of 0.75 at 25° C., soaked at room temperature for 40 minutes, filtered to remove the solution, then 150 g of distilled water was used to impregnate and wash the obtained sample for 20 minutes, and the sample was filtered to remove water. The washing was repeated in the same manner to produce a leach liquor having a pH more than 5, the sample was dried in a flowing air stream at 90° C. for 500 minutes, further heated in a high-temperature top-hat kiln for 8 hours to 1000° C., kept at 1000° C. constantly for 3 hours, and naturally cooled down to obtain Support 3.3.

Support 3.3 had a specific surface area of 1.26 m²/g, a water adsorption of 53.8% by weight, a pore volume of 0.52 ml/g, a radial crush strength of 103 N/particle, and an alkaline earth metal barium content of 0.35% by weight.

Oxalic Acid Impregnation Test

Each support sample was impregnated with an aqueous oxalic acid solution having a concentration of 0.6% by weight and having twice the weight of the support for 30 minutes, and the obtained leach liquor was analysed with Inductively Coupled Plasma Atomic Emission Spectrometry (ICP-AES). The results are summarized in Table 1.

TABLE 1

| Support | Na (μg/mL) | Si (μg/mL) | Al (μg/mL) |
|---|---|---|---|
| Support 1.1 | 69 | 166 | 162 |
| Support 1.2 | 110 | 198 | 206 |
| Support 1.3 | 82 | 161 | 230 |
| Support 2.1 | 9.5 | 18 | 19 |
| Support 2.2 | 9.4 | 19 | 18 |
| Support 2.3 | 9.8 | 19 | 19 |
| Support 2.4 | 8.5 | 15 | 22 |
| Support 2.5 | 8.8 | 14 | 21 |
| Support 2.6 | 15 | 32 | 44 |
| Support 2.7 | 9.5 | 9 | 19 |
| Support 2.8 | 9.6 | 15 | 26 |
| Support 2.9 | 9.3 | 15 | 21 |
| Support 3.1 | 50 | 169 | 161 |
| Support 3.2 | 38 | 62 | 75 |
| Support 3.3 | 26 | 43 | 65 |

Preparation for Impregnation Solution

Silver Oxalate 500 g of silver nitrate was dissolved into 540 ml of deionized water. 232 g of ammonium oxalate was dissolved into 180 ml of deionized water at 50° C. These two solutions were mixed under a violent stirring to form a white silver oxalate precipitate, aged for 60 minutes, and filtered. The precipitate was washed with deionized water until no nitrate ion existed, and cold-dried to form silver oxalate powders containing 62.6% by weight of silver and about 12% by weight of water.

Impregnation Solution X

To a glass flask with a stirrer were added 38.3 g of ethylene diamine, 14.0 g of ethanolamine and 61.0 g of deionized water to form a mixed solution. 83.0 g of the above silver oxalate powders were slowly added to the mixed solution with stirring. The solution was maintained at a temperature ranging from 0° C. to 15° C. until silver oxalate was dissolved completely. Then 0.250 g of cesium sulfate, 0.245 g of strontium acetate, 0.075 g of ammonium perrhenate, 0.072 g of ceric sulfate tetrahydrate ($Ce(SO_4)_2 \cdot 4H_2O$) and deionized water were added so that the total weight of the solution reached 200 g. The obtained solution was mixed homogenously to form a silver-containing Impregnation Solution X for use.

Impregnation Solution Y

To a glass flask with a stirrer were added 37.5 g of ethylene diamine, 13.1 g of ethanolamine and 60.0 g of deionized water to form a mixed solution. 83.0 g of the above silver oxalate powders were slowly added to the mixed solution with stirring. The solution was maintained at a temperature ranging from 0° C. to 15° C. until silver oxalate was dissolved completely. Then 0.170 g of cesium sulfate, 0.25 g of strontium acetate, 0.150 g of ammonium perrhenate, 0.075 g of ammonium molybdate tetrahydrate (($NH_4)_6Mo_7O_{24} \cdot 4H_2O$) and deionized water were added so that the total weight of the solution reached 200 g. The obtained solution was mixed homogenously to form a silver-containing Impregnation Solution Y for use.

Impregnation Solution Z

To a glass flask with a stirrer were added 35.0 g of ethylene diamine, 12.0 g of ethanolamine and 60.0 g of deionized water to form a mixed solution. 77.0 g of the above silver oxalate powders were slowly added to the mixed solution with stirring. The solution was maintained at a temperature ranging from 0° C. to 15° C. until silver oxalate was dissolved completely. Then 0.220 g of cesium sulfate, 0.250 g of strontium acetate, 0.240 g of ammonium perrhenate, 0.120 g of ammonium molybdate tetrahydrate (($NH_4)_6Mo_7O_{24} \cdot 4H_2O$), 0.048 g of lithium sulfate and deionized water were added so that the total weight of the solution reached 200 g. The obtained solution was mixed homogenously to form a silver-containing Impregnation Solution Z for use.

Preparation for Catalyst

Catalyst 1.1.1

10 g of Support 1.1 was placed into a vessel that can be vacuumed, vacuumed to an absolute pressure below 10 mmHg, 20 g of the above silver-containing Impregnation Solution X was fed to immerge the support. The sample was maintained for 30 minutes, filtered to remove the redundant solution, then heated in an air stream at 250° C. for 5 minutes, and cooled down to form Catalyst 1.1.1, which was determined to have a silver content of 18.2% by weight of the silver catalyst.

Catalyst 1.2.1

30 g of Support 1.2 was placed into a vessel that can be vacuumed, vacuumed to an absolute pressure below 10 mmHg, 60 g of the above silver-containing Impregnation Solution Y was fed to immerge the support. The sample was maintained for 30 minutes, filtered to remove the redundant solution, then heated in an air stream at 250° C. for 5 minutes, and cooled down to form Catalyst 1.2.1, which was determined to have a silver content of 18.9% by weight of the silver catalyst.

Catalyst 1.3.1

20 g of Support 1.3 was placed into a vessel that can be vacuumed, vacuumed to an absolute pressure below 10 mmHg, 40 g of the above silver-containing Impregnation Solution Z was fed to immerge the support. The sample was maintained for 30 minutes, filtered to remove the redundant solution, then heated in an air stream at 280° C. for 5 minutes, and cooled down to form Catalyst 1.3.1, which was determined to have a silver content of 17.6% by weight of the silver catalyst.

Catalyst 1.3.2

15 g of Support 1.3 was placed into a vessel that can be vacuumed, vacuumed to an absolute pressure below 10 mmHg, 30 g of the above silver-containing Impregnation Solution Z was fed to immerge the support. The sample was maintained for 30 minutes, filtered to remove the redundant solution, then heated in an air stream at 250° C. for 5 minutes, and cooled down to form Catalyst 1.3.2, which was determined to have a silver content of 17.4% by weight of the silver catalyst.

Catalyst 2.1.1

10 g of Support 2.1 was placed into a vessel that can be vacuumed, vacuumed to an absolute pressure below 10 mmHg, 20 g of the above silver-containing Impregnation Solution X was fed to immerge the support. The sample was maintained for 30 minutes, filtered to remove the redundant solution, then heated in an air stream at 250° C. for 5 minutes, and cooled down to form Catalyst 2.1.1, which was determined to have a silver content of 18.3% by weight of the silver catalyst.

Catalyst 2.2.1

10 g of Support 2.2 was placed into a vessel that can be vacuumed, vacuumed to an absolute pressure below 10 mmHg, 20 g of the above silver-containing Impregnation Solution X was fed to immerge the support. The sample was maintained for 30 minutes, filtered to remove the redundant solution, then heated in an air stream at 250° C. for 5 minutes, and cooled down to form Catalyst 2.2.1, which was determined to have a silver content of 18.1% by weight of the silver catalyst.

Catalyst 2.3.1

10 g of Support 2.3 was placed into a vessel that can be vacuumed, vacuumed to an absolute pressure below 10 mmHg, 20 g of the above silver-containing Impregnation Solution X was fed to immerge the support. The sample was maintained for 30 minutes, filtered to remove the redundant solution, then heated in an air stream at 250° C. for 5 minutes, and cooled down to form Catalyst 2.3.1, which was determined to have a silver content of 18.3% by weight.

Catalyst 2.4.1

20 g of Support 2.4 was placed into a vessel that can be vacuumed, vacuumed to an absolute pressure below 10 mmHg, 40 g of the above silver-containing Impregnation Solution Y was fed to immerge the support. The sample was maintained for 30 minutes, filtered to remove the redundant solution, then heated in an air stream at 250° C. for 5 minutes, and cooled down to form Catalyst 2.4.1, which was determined to have a silver content of 19.1% by weight of the silver catalyst.

Catalyst 2.5.1

20 g of Support 2.5 was placed into a vessel that can be vacuumed, vacuumed to an absolute pressure below 10 mmHg, 40 g of the above silver-containing Impregnation Solution Y was fed to immerge the support. The sample was maintained for 30 minutes, filtered to remove the redundant solution, then heated in an air stream a 250° C. for 5 minutes, and cooled down to form Catalyst 2.5.1, which was determined to have a silver content of 19.0% by weight of the silver catalyst.

Catalyst 2.6.1

20 g of Support 2.6 was placed into a vessel that can be vacuumed, vacuumed to an absolute pressure below 10 mmHg, 40 g of the above silver-containing Impregnation Solution Y was fed to immerge the support. The sample was maintained for 30 minutes, filtered to remove the redundant solution, then heated in an air stream at 250° C. for 5 minutes, and cooled down to form Catalyst 2.6.1, which was determined to have a silver content of 19.2% by weight of the silver catalyst.

Catalyst 2.7.1

20 g of Support 2.7 was placed into a vessel that can be vacuumed, vacuumed to an absolute pressure below 10 mmHg, 40 g of the above silver-containing Impregnation Solution Z was fed to immerge the support, maintained for 30 minutes, filtered to remove the redundant solution, then heated in an air stream at 280° C. for 5 minutes, and cooled down to form Catalyst 2.7.1, which was determined to have a silver content of 17.5% by weight of the silver catalyst.

Catalyst 2.8.1

20 g of Support 2.8 was placed into a vessel that can be vacuumed, vacuumed to an absolute pressure below 10 mmHg, 40 g of the above silver-containing Impregnation Solution Z was fed to immerge the support. The sample was maintained for 30 minutes, filtered to remove the redundant solution, then heated in an air stream at 280° C. for 5 minutes, and cooled down to form Catalyst 2.8.1, which was determined to have a silver content of 17.7% by weight of the silver catalyst.

Catalyst 2.9.1

15 g of Support 2.9 was placed into a vessel that can be vacuumed, vacuumed to an absolute pressure below 10 mmHg, 30 g of the above silver-containing Impregnation Solution Z was fed to immerge the support. The sample was maintained for 30 minutes, filtered to remove the redundant solution, then heated in an air stream at 250° C. for 5 minutes, and cooled down to form Catalyst 2.9.1, which was determined to have a silver content of 17.5% by weight of the silver catalyst.

Catalyst 3.1.1

10 g of Support 3.1 was placed into a vessel that can be vacuumed, vacuumed to an absolute pressure below 10 mmHg, 20 g of the above silver-containing Impregnation Solution X was fed to immerge the support. The sample was maintained for 30 minutes, filtered to remove the redundant solution, then heated in an air stream at 250° C. for 5 minutes, and cooled down to form Catalyst 3.1.1, which was determined to have a silver content of 18.1% by weight of the silver catalyst.

Catalyst 3.2.1

30 g of Support 3.2 was placed into a vessel that can be vacuumed, vacuumed to an absolute pressure below 10 mmHg, 60 g of the above silver-containing Impregnation Solution Y was fed to immerge the support. The sample was maintained for 30 minutes, filtered to remove the redundant solution, then heated in an air stream at 250° C. for 5 minutes, and cooled down to form Catalyst 3.2.1, which was determined to have a silver content of 19.3% by weight of the silver catalyst.

Catalyst 3.3.1

20 g of Support 3.3 was placed into a vessel that can be vacuumed, vacuumed to an absolute pressure below 10 mmHg, 40 g of the above silver-containing Impregnation Solution Z was fed to immerge the support, maintained for 30 minutes, filtered to remove the redundant solution, then heated in an air stream at 280° C. for 5 minutes, and cooled down to form Catalyst 3.3.1, which was determined to have a silver content of 17.3% by weight of the silver catalyst.

The above sample catalysts had the promoter contents as shown in Table 2.

TABLE 2

| Catalyst | Cs (ppm) | Sr (ppm) | Re (ppm) | Ce (ppm) | Mo (ppm) | Li (ppm) |
|---|---|---|---|---|---|---|
| 1.1.1 | 619 | 397 | 195 | 86 | | |
| 1.2.1 | 514 | 407 | 382 | | 151 | |
| 1.3.1 | 637 | 412 | 608 | | 241 | 29 |
| 1.3.2 | 637 | 412 | 608 | | 241 | 29 |
| 2.1.1 | 624 | 396 | 201 | 86 | | |
| 2.2.1 | 601 | 401 | 198 | 82 | | |
| 2.3.1 | 615 | 399 | 190 | 88 | | |
| 2.4.1 | 501 | 403 | 384 | | 153 | |
| 2.5.1 | 518 | 411 | 374 | | 149 | |
| 2.6.1 | 509 | 404 | 379 | | 154 | |
| 2.7.1 | 639 | 415 | 617 | | 237 | 30 |
| 2.8.1 | 642 | 409 | 623 | | 246 | 27 |
| 2.9.1 | 636 | 417 | 619 | | 238 | 31 |
| 3.1.1 | 623 | 403 | 193 | 84 | | |
| 3.2.1 | 516 | 415 | 378 | | 147 | |
| 3.3.1 | 645 | 418 | 623 | | 249 | 32 |

Under the standard evaluation conditions given in the above section of "Catalyst Performance Evaluation" and with the space velocity and the ethylene oxide concentration as shown in Table 3, all of the sample catalysts were evaluated and compared. The results are summarized in Table 3.

TABLE 3

| Example | Space velocity/ h⁻¹ | Concentration of ethylene oxide in the effluent from the reactor/ mol % | Day 3 | | Day 7 | | Day 14 | | Day 30 | | Day 120 | |
|---|---|---|---|---|---|---|---|---|---|---|---|---|
| | | | Reaction Temperature (°C.) | Selectivity (%) | Reaction Temperature (°C.) | Selectivity (%) | Reaction Temperature (°C.) | Selectivity (%) | Reaction Temperature (°C.) | Selectivity (%) | Reaction Temperature (°C.) | Selectivity (%) |
| 1.1.1 | 5000 | 2.45 | | | 242 | 83.3 | 244 | 83.7 | | | | |
| 3.1.1 | 5000 | 2.45 | | | 236 | 82.1 | 242.2 | 82.6 | | | | |
| 1.2.1 | 5000 | 2.45 | | | 234.1 | 81.8 | 236.1 | 82.2 | 239 | 82.5 | | |
| 3.2.1 | 5000 | 2.45 | | | 235.1 | 82.7 | 236 | 83 | 236.8 | 83.2 | | |
| 2.1.1 | 5000 | 2.45 | | | 235 | 84.5 | 242 | 85.1 | | | | |
| 2.2.1 | 5000 | 2.45 | | | 236.8 | 83.8 | 241.5 | 85 | | | | |
| 2.3.1 | 5000 | 2.45 | | | 234.3 | 84.1 | 236 | 84.3 | | | | |
| 2.4.1 | 5000 | 2.45 | | | 233.2 | 84 | 234 | 85.3 | 236.2 | 85.4 | | |
| 2.5.1 | 5000 | 2.45 | | | 230 | 83.6 | 231.6 | 84.5 | 233.7 | 84.6 | | |
| 2.6.1 | 5000 | 2.45 | | | 232.4 | 83.6 | 233.9 | 84.2 | 235 | 84.7 | | |
| 2.7.1 | 7000 | 2.5 | 237.5 | 84.1 | 238.7 | 84.5 | 241.5 | 85 | 242.2 | 85.6 | | |
| 2.8.1 | 7000 | 2.5 | 238.2 | 84 | 239.1 | 84.6 | 242 | 84.9 | 243 | 85.5 | | |
| 1.3.1 | 7000 | 2.5 | 241.8 | 83.8 | 243 | 83.8 | 245.8 | 83.8 | 245.4 | 84.3 | | |
| 1.3.2 | 4500 | 2.5 | | | 227.6 | 83.8 | 228.3 | 83.9 | 233.7 | 84.6 | 240 | 86.8 |
| 3.3.1 | 4500 | 2.5 | | | 238.6 | 84.3 | 243.3 | 84.7 | 249.7 | 85.1 | 255 | 84.5 |
| 2.9.1 | 4500 | 2.5 | | | 227.6 | 85.2 | 229 | 85.2 | 231 | 85.4 | 239 | 87.5 |

What is claimed is:

1. A process for preparing an alumina support, comprising:
 (a) mixing at least one alumina starting material, at least one alkaline earth metal salt, optionally at least one carbonaceous burnout material, optionally at least one fluoride, at least one binder and water to produce a mixture,
 wherein the alumina starting material comprises alpha-alumina trihydrate and pseudo-boehmite in a weight ratio of alpha-alumina trihydrate to pseudo-boehmite ranging from 0,5:1 to 5:1, and
 wherein based on the total weight of the alumina starting material,
 the alkaline earth metal salt is in an amount ranging from 0.05% to 3.0% by weight, calculated based on the alkaline earth metal,
 the carbonaceous burnout material is in an amount ranging from 0% to 30% by weight,
 the fluoride is in an amount ranging from 0% to 3% by weight, and
 the binder and water are in a total amount ranging from 10% to 40% by weight;
 (b) extruding the mixture obtained in step (a) to form shaped entities;
 (c) drying the shaped entities obtained in step (b) at a temperature ranging from 60° C. to 200° C.;
 (d) calcining the shaped entities obtained in step (c) at a temperature ranging from 1100° C. to 1600° C. to convert to a semi-finished alpha-alumina support;
 (e) treating the semi-finished alpha-alumina support obtained in step (d) with a thermally decomposable organic acid solution having a pH of no more than 2.5;
 (f) washing the treated support obtained in step (e) with water to produce a leach liquor having a pH of more than 5 and a water-washed product: and
 (g) heat-treating the water-washed product obtained in step (f) at a temperature ranging from 80° C. to 1200° C.

2. The process according to claim 1, wherein the thermally decomposable organic acid solution having a pH of no more than 2.5 used in step (e) is substantially free of fluorine.

3. The process according to claim 1, wherein in step (e), the thermally-decomposable organic acid solution having a pH of no more than 2.5 is used in such an amount that the semi-finished alpha-alumina support can be fully immersed therein.

4. The process according to claim 1, wherein the at least one carbonaceous burnout material is chosen from petroleum coke, carbon powder, graphite, polyethylene, polypropylene, rosin, and vaseline.

5. The process according to claim 1, wherein the at least one alkaline earth metal salt is chosen from salts of barium, magnesium, calcium and/or strontium.

6. The process according to claim 1, wherein the at least one fluoride is chosen from aluminum fluoride and ammonium fluoride.

7. The process according to claim 1, wherein the at least one binder is chosen from nitric acid and acetic acid.

8. The process according to claim 1, wherein a portion or all of the alpha-alumina trihydrate is replaced by a substituting alumina powder, which has been pre-calcined into alpha-alumina or a transition alumina; a portion or all of the pseudo-boehmite is replaced by an alumina sol; the ratio of the total weight of alpha-alumina trihydrate and its substitute if present to the total weight of pseudo-boehmite and its substitute if present ranges from 0.5:1 to 5:1.

9. The process according to claim 8, wherein the ratio of the total weight of alpha-alumina trihydrate and its substitute if present to the total weight of pseudo-boehmite and its substitute if present ranges from 1:1 to 4:1.

10. The process according to claim 1, wherein the thermally decomposable organic acid solution comprises at least one thermally decomposable organic acid chosen from formic acid, acetic acid, propionic acid, butyric acid, oxalic acid, benzoic acid, and phenol.

11. The process according to claim 10, wherein the at least one thermally decomposable organic acid is chosen from formic acid, acetic acid, and oxalic acid.

12. The process according to claim 1, wherein in step (g), the water-washed product obtained in step (f) is heat-treated at a temperature ranging from 260° C. to 1200° C.

13. The process according to claim 1, wherein in step (g), the water-washed product obtained in step (f) is heat-treated at a temperature ranging from 1000° C. to 1200° C.

* * * * *